United States Patent [19]

Nagaya et al.

[11] Patent Number: 4,891,574
[45] Date of Patent: Jan. 2, 1990

[54] HYGROMETER WITH PLURAL MEASURING BONES AND REDUNDANCY SYSTEM CIRCUIT

[75] Inventors: Kazuhiko Nagaya, Tokyo; Hiroshi Sakurai, Yokohama, both of Japan; Andrew K. Michell, Cambridge, England

[73] Assignees: Mitchell Instruments Ltd., Cambridge, England; Kabushiki Kaishia Tekune Yohkoh, Tokyo, Japan

[21] Appl. No.: 287,099

[22] Filed: Dec. 20, 1988

[30] Foreign Application Priority Data

Dec. 23, 1987 [JP] Japan ................. 62-325797

[51] Int. Cl.$^4$ ............................ G01R 27/26
[52] U.S. Cl. ...................... 324/61 P; 73/336.5; 340/522; 340/602
[58] Field of Search ............. 324/61 R, 61 P, 65 R, 324/65 P; 73/335, 336, 336.5; 340/602, 601, 522, 521, 523; 200/61.04, 61.05; 338/35

[56] References Cited

U.S. PATENT DOCUMENTS

| 2,834,201 | 5/1958 | Ohlheiser | 324/65 P |
| 3,045,198 | 7/1962 | Dolan et al. | 324/65 P |
| 3,872,419 | 3/1975 | Groves et al. | 340/602 X |
| 4,401,976 | 8/1983 | Stadelmayr | 340/522 |
| 4,662,220 | 5/1987 | Laue | 73/336.5 |

Primary Examiner—Reinhard J. Eisenzopf
Assistant Examiner—Robert W. Mueller
Attorney, Agent, or Firm—Jeffers, Hoffman & Niewyk

[57] ABSTRACT

A hygrometer of the electrical impedance type includes a sensing element (1) having a porous moisture adsorbing layer (3), the electrical properties of which vary with the quantity of water vapour adsorbed on it sandwich between a substrate (2) and a porous conducting electrode (4). The conducting electrode (4) is divided into a number of separate measuring zones (6A, 6 and 6C) by gaps (5). The hygrometer also includes a redundancy system circuit (7) which is connected to each of the separate measuring zones (6A, 6B and 6C) and which only provides a moisture indication when the output from at least two of the zones (6A, 6B and 6C) are in agreement. This arrangement enables failures of the sensing element (1) to be detected and distinguished from a false moisture indication.

15 Claims, 4 Drawing Sheets

Fig.6.
Fig.7.
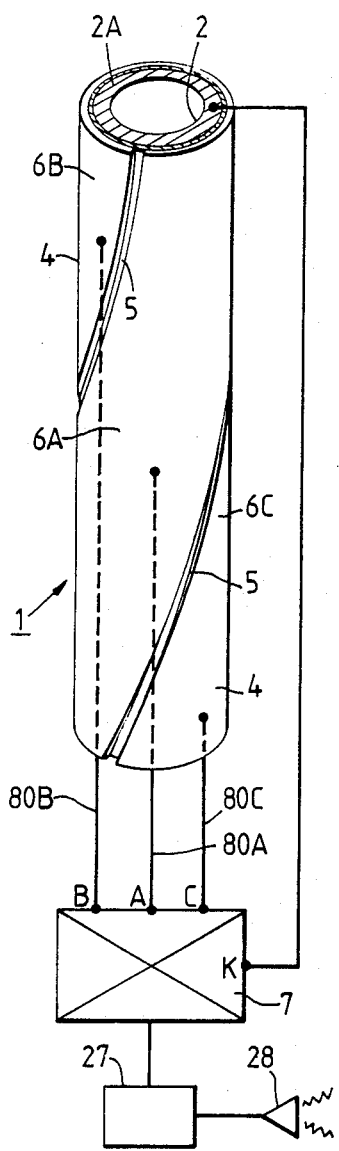
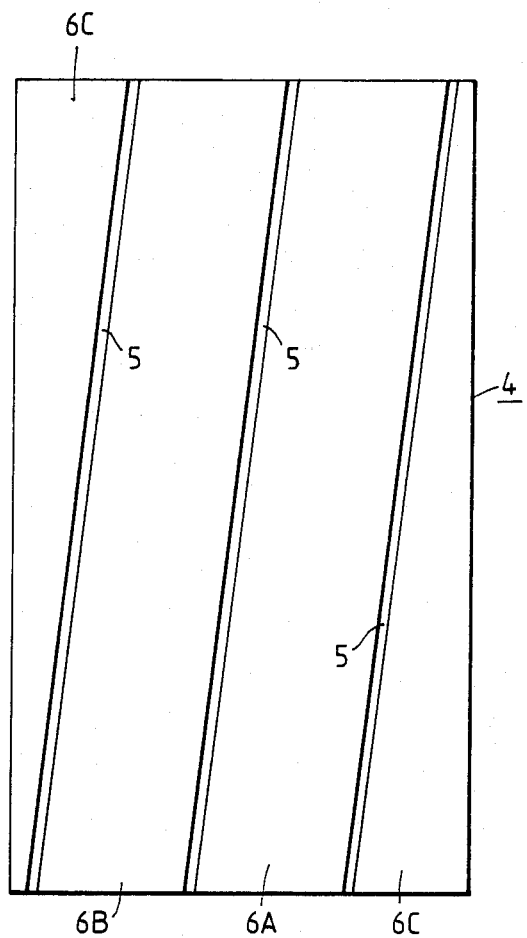

HYGROMETER WITH PLURAL MEASURING BONES AND REDUNDANCY SYSTEM CIRCUIT

BACKGROUND OF THE INVENTION

This invention relates to hygrometers or humidity sensors of the electrical impedance type which are used for measuring continuously the dewpoint of a gas or gas mixture.

Conventionally the detection and measurement of humidity is performed at a single location using an electrical impedance type of hygrometer. The sensing element of such a hygrometer typically comprises a substrate formed of aluminium on which a porous aluminium oxide film is formed by anodic oxidation. This porous aluminium oxide film is then covered by a porous conducting electrode. Water vapour from the atmosphere surrounding the sensor element is adsorbed onto the porous aluminium oxide layer and its electrical properties such as its dielectric constant and its resistance vary with the quantity of water vapour adsorbed onto it. As the electrical properties of the porous aluminium oxide layer vary so does the impedance of the sensing element. The hygrometer includes a sensing circuit which measures the electrical impedance of the sensing element and produces an output indicative of the absolute, or percentage humidity of the atmosphere surrounding the sensor element. It is also known to use other materials such as silicon for the substrate.

As a result of the hygrometer relying upon a change in the electrical impedance of the sensing element to determine the humidity of the atmosphere surrounding it any change in the electrical characteristics of the sensing element, for example as a result of ageing or corrosion, which is not directly attributable to a change in the humidity will give rise to a flase indication of the humidity.

SUMMARY OF THE INVENTION

According to this invention such a hygrometer has its conducting electrode divided into a number of separate measuring zones and the hygrometer includes a redundancy system circuit which receives separate outputs one from each of the respective measuring zones and only produces an output indication of the humidity when the output from at least two of the separate measuring zones are in agreement.

In this way the conducting surface of the sensing element may be divided into only two separate measuring zones and the redundancy system circuit be arranged to provide an output only when the humidity measurement from the two zones are in agreement with one another but, preferably, the conducting electrode surface is divided into an odd number of measuring zones and the redundancy system circuit provides an output corresponding to the humidity measurement provided by the majority of the measuring zones.

The substrate of the sensing element may be generally cylindrical and, in this case its conducting electrode may be divided in the axially extending direction into a number of circumferentially separated measuring zones, may be divided helically into a number of helically extending measuring zones or may be divided into a number of circumferentially extending zones which are axially separated from one another along the length of the cylindrical substrate. Alternatively, the substrate may be substantially flat.

BRIEF DESCRIPTION OF THE DRAWINGS

Various examples of hygrometers in accordance with this invention will now be described with reference to the accompanying drawings, in which:

FIG. 6 is a diagrammatic view of a second example;

FIG. 7 is a developed side elevation of the sensing element used in the second example;

DESCRIPTION OF THE PREFERRED EXAMPLES

Figure 1:
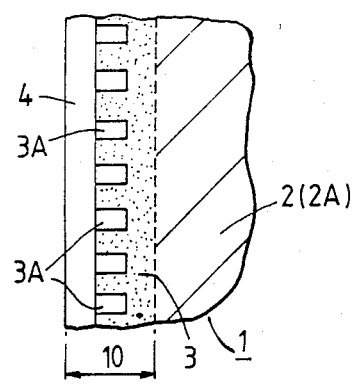
FIG. 1 is a very much enlarged scrap longitudinal sectiont through part of the first example.
Figure 2:
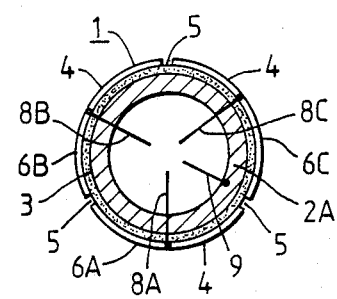
FIG. 2 is a cross-section through part of the sensing element.
Figure 3:
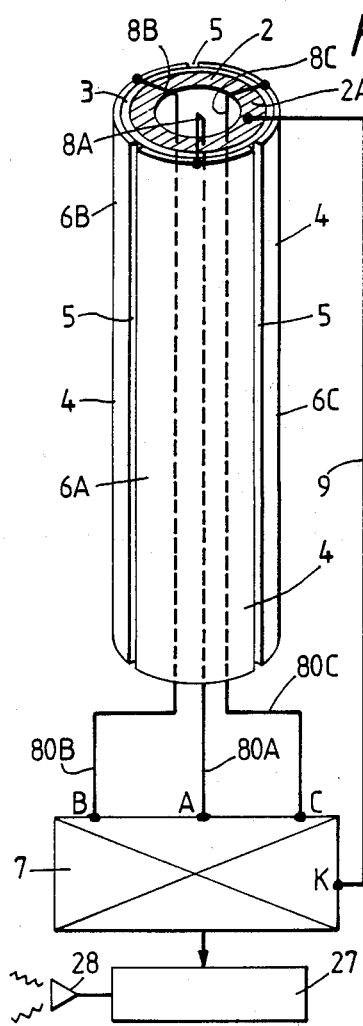
FIG. 3 is a diagram illustrating the principle of the first example.

The first example of electrical impedance type hygrometer comprises a generally cylindrical main body 1 having a substrate 2 formed of aluminium in the form of a hollow cylinder which constitutes a common electrode 2A. A porous dielectric moisture adsorbative layer 3 is provided on the outer surface of the substrate 2 and includes adsorbative recesses 3A. The adsorbative layer 3 is formed of highly insulating porous aluminium oxide formed by anodic oxidation of the surface of the substrate 2. The dielectric constant and resistance of the porous aluminium oxide layer 3 vary as water vapour molecules are adsorbed and desorbed from it. The quantity of water vapour adsorbed onto the porous aluminium oxide film depends upon the humidity of the atmosphere surrounding it. A porous conducting electrode 4 comprising a thin film of gold or other material is vapour coated onto the outside of the porous aluminium oxide layer 3. Thus, the sensing element of the hygrometer is constructed as an electrical capacitor with the substrate 2 and electrode 4 forming its electrodes and the porous aluminium oxide layer 3 which is sandwiched between the two electrodes forming the dielectric layer. Typically the aluminium oxide layer 3 and the electrode 4 are each formed to have a thickness of the order of tens or several tens of microns. Longitudinally extending gaps 5 are equiangularly spaced around the sensing element and formed by regions in which the conducting electrode 4 is absent. The gaps 5 may be formed by depositing the conducting electrode 4 only on the region of the surface of the porous aluminium oxide layer 3 where it is required or, alternatively, the electrode 4 may be provided over the entire surface of the porous aluminium oxide layer and then the gaps 5 formed by an etching step to remove the conducting electrode 4 from the regions of the gap 5. The conducting electrode 4 is divided into three separate measuring zones 6A, 6B and 6C all having the same area. Typically the area of each of the zones 6A, 6B, and 6C is substantially the same as the area of a conventional hygrometer sensing element.

The hygrometer also includes a redundancy system circuit 7 and the measuring zones 6A, 6B and 6C are connected to the redundancy system circuit 7 by connecting leads 8A, 8B and 8C having signal ines 80A, 80B and 80C. The substrate 2 forming the common electrode 2A is also connected to the redundancy circuit 7 by a lead 9.

Figure 4:
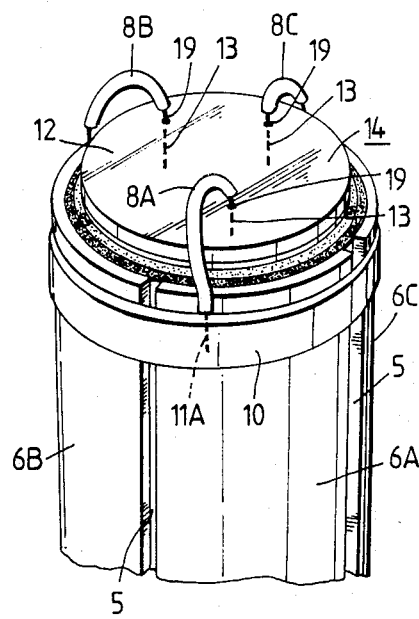
FIG. 4 is a perspective view of the top of the sensing element of the first example.
Figure 5:
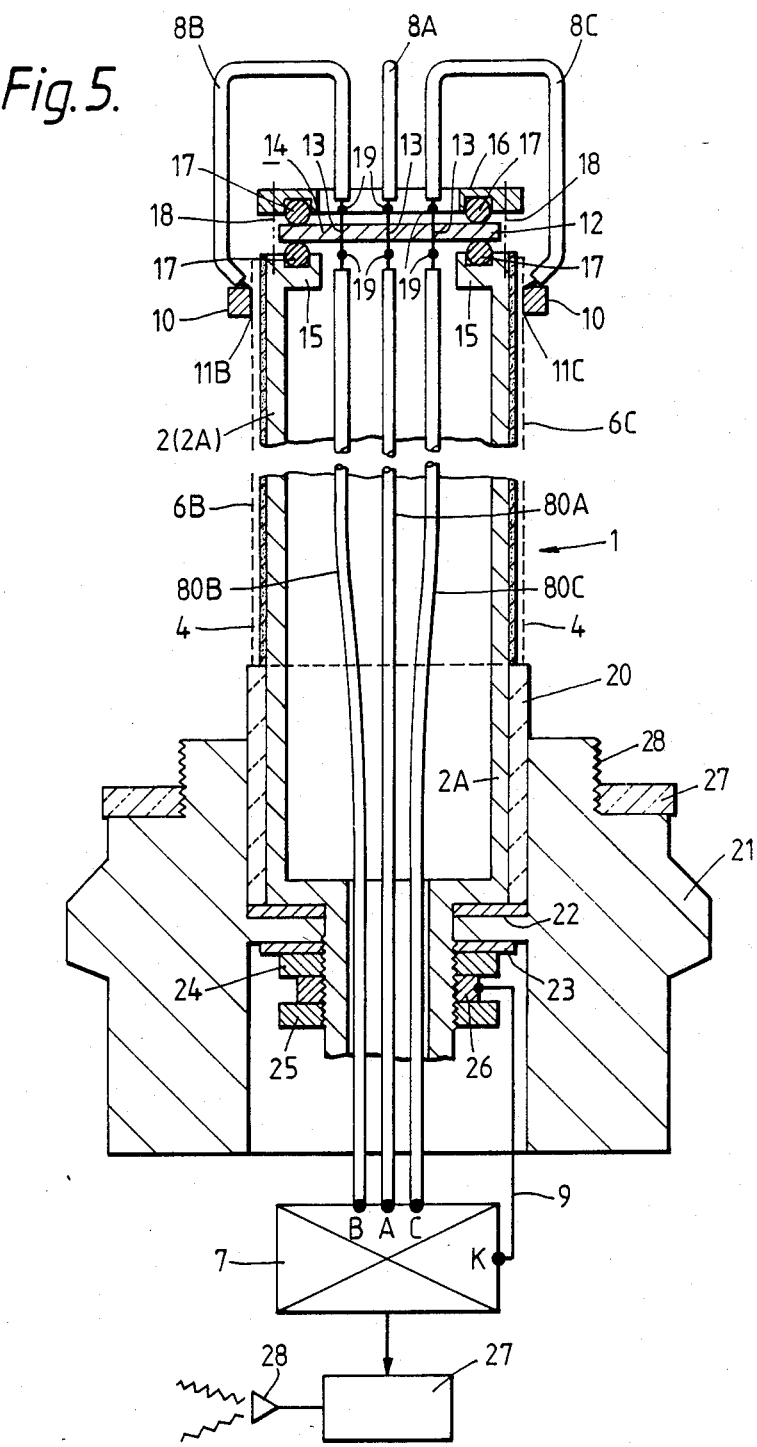
FIG. 5 is a detailed longitudinal sectional elevation through the sensing element of the first example.
Figure 8:
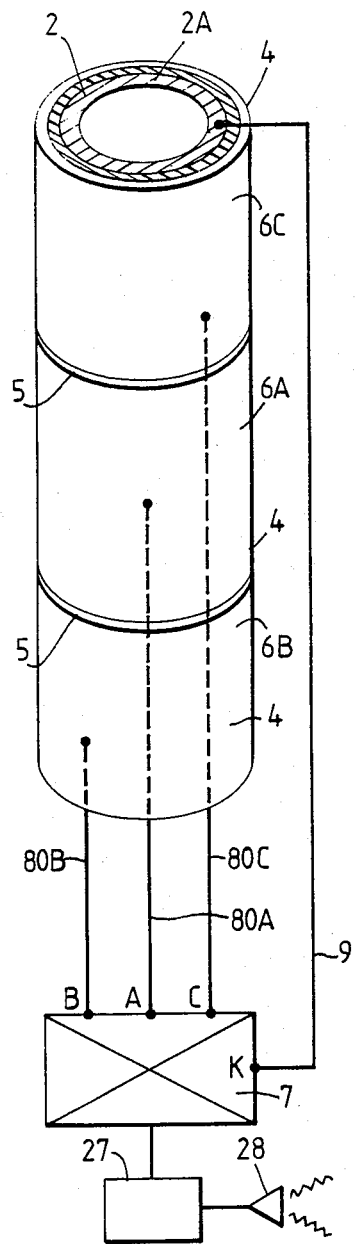
FIG. 8 is a diagram of the third example.

FIGS. 4 and 5 illustrate the specific manner in which the insulated electrical leads 8A, 8B and 8C are connected to their respective measuring zones 6A, 6B and 6C. Bared end portions of the leads 11A are held in contact with the conducting electrode 4 of each of the zones 6A, 6B and 6C by an insulating band 10 of silicone rubber or polytetrafluoroethylene. The insulated leads 8A, 8B and 8C are connected to leadthroughs 13 which are hermetically sealed into a glass or ceramic plate 14 which is clamped to the upper end, as shown in FIGS. 4 and 8, of the sensing element. The upper end of the substrate 2 includes an inwardly directed flange 15 and the plate 14 is sandwiched between O-ring seals 17 and 18 and an annular plate 16 which is clamped to the flange 15 by screw threaded fastenings 18 (not shown in detail). Alternatively the plate 14 may be connected by brasing or adhesive. At the lower end of the main body of the sensing element an insulating sleeve 20 insulates the substrate 2 and conducting electrode 4 from a metallic mount 21. The main body 1 is also electrically insulated from the mount 21 by polytetrafluorethylene rings 22 and 23 and held in position by clamping nuts 24 and 25 which are secured to a screw threaded spiggot formed integrally with the aluminium sleeve 2. The connecting lead 9 is connected to the terminal ring 26 and clamped between the two clamping nuts 24 and 25.

The redundancy system circuit 7 is preferably capable of operating in a number of separate modes such as a parallel mode, in which all three zones 6A, 6B and 6C are monitored in parallel, a two out of three mode in which the outputs of only two of the three zones 6A, 6B and 6C are used to provide an output signal and two/three decision by majority mode in which when there is a difference in the outputs from the zones 6A, 6B and 6C the redundancy circuit selects the two outputs that are similar and provides an output in accordance with them. An electrical impedance measuring device 27 provides an output (not shown) which is dependent upon the impedance of the capacitor formed by the substrate 2, electrode 4 and dielectric 3, and is calibrated to provide an indication of the humidity of the atmosphere surrounding the sensor element 1. An alarm indicator 28 provides a first indication in the event that the output of one of the zones 6A, 6B and 6C differs from that of the others so that the output of the device is given taking into accound the output of only two of the three measuring zones 6A, 6B and 6C. The alarm device 28 has a second alarm indication when the outputs from all three zones 6A, 6B and 6C are different so that, no effective output indicative of the humidity is provided by the device.

Thus, when any pair of the measuring zones 6A, 6B and 6C indicate respective measurements which are substantially equal to each other, within an allowable tolerance, and the remaining one indicates a measurement difference from these two values, an output signal from the redundancy system circuit 7 corresponding to the two equal values is displayed with an output of the electrical measuring device 27. However, if all three measuring zones 6A, 6B and 6C indicate respective measurements which are different from one another no output signal is provided from the electrical impedance measuring device 27 and the second output of the alarm 28 will be activated. The alarm 28 may be implemented in the form of a red warning lamp, in the form of an audible alarm or one for each alarm state.

In the first example the gaps 5 extend longitudinally to divide the electrode 4 into three separate longitudinally extending panels each of which subtends an equal angle at the axis of the substrate. The difference between the examples in accordance with this invention lies only in the form of their sensing element 1 and in the way in which the conducting electrodes 4 of the sensing elements 1 are divided. Thus, in the second example shown in FIGS. 6 and 7 the grooves 5 are helical and divide the conducting electrode 4 into three helically extending panels 6A, 6B and 6C. In the third example the gaps 5 extend circumferentially and so divide the conducting electrode 4 into three longitudinally spaced rings.

Figure 9:
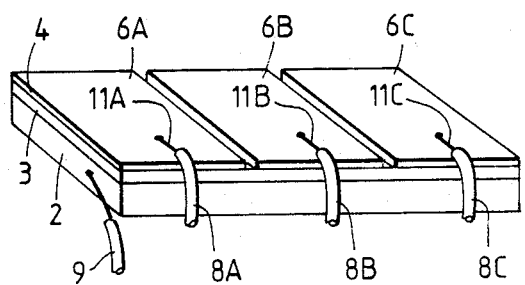
FIG. 9 is a perspective view of a fourth example of sensor element.

In the fourth example illustrated in FIG. 9 the aluminium substrate 2 is formed by a flat plate having porous aluminium oxide 3 deposited on one face and the conducting electrode 4 deposited on top of the porous aluminium oxide layer 3. The substrate 2 is generally rectangular and the gaps 5 divide the conducting electrode 4 into three zones 6A, 6B and 6C of substantially equal area.

Since in accordance with the present invention the surface of the conducting electrode 4 is divided into a number of separate measuring zones 6A, 6B and 6C the respective signals from which are input into the redundancy system circuit 7 it is possible to provide the number of separate sensing elements without substantially increasing the size or volume of the hygrometer. Additionally, by providing a number of different sensors at one and the same location it is possible to detect a fault in the hygrometer and average out the signal from more than one sensing element to provide a more reliable humidity measurement. The provision of a number of separate measuring zones on the same sensing element improves the useful life of the hygrometer since it can still work effectively provided that at least two of the zones are operating correctly and giving a substantially similar indication and so can continue to operate even after one of the zones 6A, 6B and 6C has failed.

We claim:

1. In a hygrometer of the electrical impedance type comprising a sensing element including an electrically conducting substrate, a porous moisture adsorbing layer the electrical properties of which vary with the quantity of water vapour adsorbed onto it formed on said electrically conducting substrate, and a porous conducting electrode formed on top of porous moisture adsorbing layer; the improvement wherein said porous conducting electrode is divided into a number of separate measuring zones and said hygrometer also includes a redundancy system circuit, said redundancy system circuit receiving separate outputs one from each of said respective measuring zones and only produces an output indicative of the humidity when said outputs from at least two of said separate zones are in agreement.

2. The hygrometer of claim 1, wherein said conducting electrode is divided into an odd number of measuring zones and wherein said redundancy system circuit provides a humidity output dependent upon said output of a majority of said measuring zones.

3. The hygrometer of claim 1, which also includes an alarm device and wherein said redundancy circuit is arranged to trigger said alarm device in the event that said outputs from all of said measuring zones are different.

4. The hygrometer of claim 1, wherein said conducting electrode is divided into three separate measuring zones and wherein said redundancy system circuit provides an output corresponding to the signals from whichever two of said three measuring zones are substantially equal.

5. The hygrometer of claim 1, wherein said substrate is cylindrical.

6. The hygrometer of claim 5, wherein said measuring zones extend longitudinally along an outside face of said cylindrical substrate and subtend an equal angle at an axis of said cylindrical substrate.

7. The hygrometer of claim 5, wherein said measuring zones extend helically around an outside face of said cylindrical substrate.

8. The hygrometer of claim 5, wherein said measuring zones have the form of a number of longitudinally separated rings formed on an outside surface of said cylindrical substrate.

9. The hygrometer of claim 1, wherein said substrate is substantially flat.

10. In the hygrometer of the electrical impedance type comprising a sensing element including an electrically conducting substrate, a porous moisture adsorbing layer the electrical properties of which vary with the quantity of water vapour adsorbed onto it formed on said electrically conducting substrate, and a porous conducting electrode formed on top of said porous moisture adsorbing layer; the improvement wherein said porous conducting electrode is divided into three separate measuring zones and said hygrometer also includes a redundancy system circuit, said redundancy system circuit receiving separate outputs one from each of said respective measuring zones and producing an output corresponding to the signals from whichever two of said three capacity measuring zones are substantially equal.

11. The hygrometer of claim 10, wherein said substrate is cylindrical.

12. The hygrometer of claim 11, wherein said measuring zones extend longitudinally along an outside face of said cylindrical substrate and subtend an equal angle at an axis of said cylindrical substrate.

13. The hygrometer of claim 11, wherein said measuring zones extend longitudinally around an outside face of said cylindrical substrate.

14. The hygrometer of claim 11, wherein said measuring zones have the form of a number of longitudinally separated rings formed on an outside surface of said cylindrical substrate.

15. The hygrometer of claim 10, wherein said substrate is substantially flat.

* * * * *